(12) United States Patent
Hidaka et al.

(10) Patent No.: US 6,991,932 B2
(45) Date of Patent: *Jan. 31, 2006

(54) CARBON NANOTUBE CONNECTED INSTRUMENT

(75) Inventors: Kishio Hidaka, Hitachiota (JP);
Akihiro Miyauchi, Hitachi (JP);
Mitsuo Hayashibara, Hitachinaka (JP);
Yuji Miyahara, Kodaira (JP)

(73) Assignee: Hitachi, Ltd., Tokyo (JP)

( * ) Notice: Subject to any disclaimer, the term of this patent is extended or adjusted under 35 U.S.C. 154(b) by 280 days.

This patent is subject to a terminal disclaimer.

(21) Appl. No.: 10/378,612

(22) Filed: Mar. 5, 2003

(65) Prior Publication Data

US 2003/0156985 A1    Aug. 21, 2003

Related U.S. Application Data

(63) Continuation of application No. 09/972,934, filed on Oct. 10, 2001, now Pat. No. 6,555,362.

(30) Foreign Application Priority Data

May 30, 2001    (JP)    ............................. 2001-161584

(51) Int. Cl.
*C12M 1/34* (2006.01)
(52) U.S. Cl. ............................. 435/287.2; 435/287.3; 435/288.7; 422/82.01; 250/309; 250/311
(58) Field of Classification Search ............. 435/287.1, 435/287.2, 287.3, 288.7; 250/309, 311; 422/82.01, 422/82.05
See application file for complete search history.

(56) References Cited

U.S. PATENT DOCUMENTS

| 5,363,697 | A | 11/1994 | Nakagawa et al. |
| 5,601,982 | A | 2/1997 | Sargent et al. |
| 5,609,744 | A | 3/1997 | Zenharusern et al. |
| 5,824,470 | A | 10/1998 | Baldeschwieler et al. |
| 6,322,963 | B1 | 11/2001 | Bauer |
| 6,346,189 | B1 | 2/2002 | Dai et al. |
| 6,401,526 | B1 * | 6/2002 | Dai et al. ............ 73/105 |
| 6,457,350 | B1 * | 10/2002 | Mitchell ............ 73/105 |
| 6,708,556 | B1 * | 3/2004 | Kim et al. ............ 73/105 |

FOREIGN PATENT DOCUMENTS

GB    2235049    2/1991

* cited by examiner

*Primary Examiner*—David Redding
(74) *Attorney, Agent, or Firm*—Antonelli, Terry, Stout and Kraus, LLP.

(57) ABSTRACT

A gene sequence-reading instrument comprising attractive force-generating probes (terminals) each retaining DNA-constituting bases to carbon nanotubes, a detecting part for detecting the attractive force generated between the base sequences on RNA having gene information and said attractive force-generating probes as distortion, an amplifying part for amplifying said distortion, a recording part for recording the distortion signal from said amplifying part, and a display part for displaying base sequences of RNA based on the information recorded in said recording part.

8 Claims, 4 Drawing Sheets

CARBON NANOTUBE CONNECTED INSTRUMENT

This application is a Rule 53(b) continuation of U.S. application Ser. No. 09/972,934 filed Oct. 10, 2001, now U.S. Pat. No. 6,555,362, the subject matter of which is incorporated herein by reference.

BACKGROUND OF THE INVENTION (1) Field of the Invention

The present invention relates to a gene sequence-reading instrument for reading the four bases of A, C, G, and U of the single stranded ribonucleic acid (RNA).

(2) Description of the Related Art

In the conventional DNA sequencers, a DNA was enzymatically cleaved at specific sequence region, a fluorophore was linked to the end of the cleaved region by a synthetic reaction, DNA was allowed to migrate at one direction by electrophoresis, and the length of the DNA was estimated by a laser beam from the time required for the migration. In this method, although the base at the end portion can be identified by an enzyme used for cleaving, bases in the remaining portion are completely unknown. Thus, the method required the sequencing of the end portion by cleaving the same DNA with various enzymes, and the reconstitution of the original DNA using a large scale computer.

DNA chips utilize the property that when RNA having a known sequence is spotted on a glass substrate, and the subject DNA is contaminated into the spotted region, the subject DNA can bind to the RNA of the known sequence only when the DNA has the consensus sequence with the RNA having the known sequence. Thus, sequences were estimated by spotting a variety of RNAs of known sequences and then detecting the presence or absence of the binding to the subject DNA. In either case, the coding sequence of the subject DNA cannot be directly read.

The conventional technology of DNA sequencers and DNA chips had the problems that they required the fragmentation of the original DNA, and even if the fragmented DNA sequences were partially identified, it was not easy to restore the original DNA. Thus, the total throughput required long hours, and besides the reliability of the restored DNA sequence was questioned.

SUMMARY OF THE INVENTION

In order to solve the above problems, it is an object of the present invention to detect each of four bases A, C, G, and U in the sequence and identify the gene sequence without the need of enzymatic cleavage.

In order to achieve the above purpose, the characteristics of the present invention is to detect an attractive force generated by hydrogen bonding with only one of the four bases A, C, G, and U in the sequence of single stranded RNA for each of the four bases.

Another characteristics of the present invention is to connect carbon nanotubes consisting of a very thin bundle with a diameter of a few nanometers to the end of the probe, and nucleotides composed of a base, a sugar and a phosphate is bound by chemical modification to one end of the connected carbon nanotube. In the subject RNA sequence, the property of bases that A binds only to U, G binds only to C due to complementarity is used to identify the base by the generation of an attractive force by the binding with only a specific base.

Furthermore, another characteristics of the present invention is to detect the attractive force generated by the complementarity of bases directly above during probe scanning, and to record it as a gene information such as positional information on a two-dimensional image.

Furthermore, another characteristics of the present invention is to display all base sequences in one RNA by superimposing specific points to each of separate four bases, e.g. the above positional information on one image.

PREFERRED EMBODIMENT OF THE INVENTION

Figure 1:
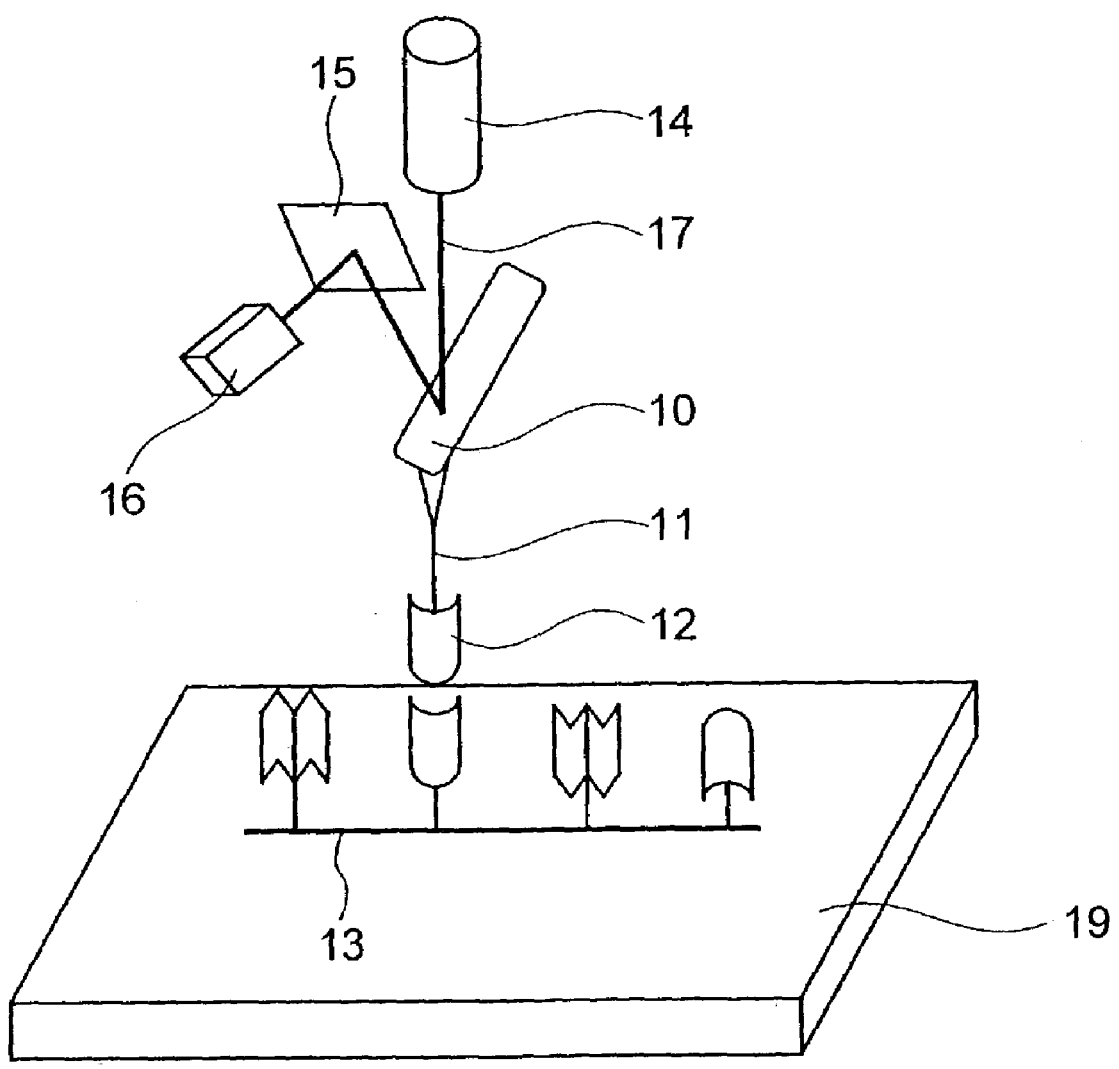
FIG. 1 is a schematic configuration of a gene sequence-reading instrument of the present invention.

The preferred embodiments of the present invention are as follows:

(1) A gene sequence-reading instrument comprising attractive force-generating probes (terminals) each securing DNA-constituting bases to carbon nanotubes, a detecting part for detecting the attractive force generated between the base sequences on RNA having gene information and said attractive force-generating probes as distortion, an amplifying part for amplifying said distortion, a recording part for recording the distortion signal from said amplifying part, and a display part for displaying base sequences of RNA based on the information recorded in said recording part.

(2) The instrument described in the above (1) wherein said attractive force-generating probe retains one of said bases through said carbon nanotube and the diameter of said carbon nanotube is smaller than the distance between the base sequences of said RNA.

(3) The instrument described in the above (1) wherein said carbon nanotube is connected to said probe part comprising a connecting material consisting mainly of a rare metal such as tungusten, nickel, iron, cobalt, or gold, or an alloy thereof.

(4) The instrument described in the above (3) wherein said probe part and said carbon nanotube is connected by means of a metal such as gold, platinum, titanium, rhenium, silicon, or tungusten, or a nitride thereof used as a connecting material.

(5) The instrument described in the above (1) wherein the chemical functional groups that modify the end of said carbon nanotube is a complex of an organic base, a sugar, and a phosphate.

(6) The instrument described in the above (1) wherein the chemical functional groups that modify the end of said carbon nanotube detects an attractive force by covalent binding with a base specific to each of the four bases of A, C, G, and U of the sequence of single stranded RNA, and the result is recorded as a position of the base on a two-dimensional image.

(7) The instrument described in the above (1) wherein the binding force of the chemical bonding of the functional groups that modify the end of said carbon nanotube to each of the four bases of A, C, G, and U of the sequence of single stranded RNA changes depending on the pH of the test solution.

(8) The instrument described in the above (1) which is designed so that 50% or more of the total length of the probe in which the end of said carbon nanotube is chemically modified may be immersed in the test solution.

(9) The instrument described in the above (8) wherein said probe has an exterior pressing device that utilizes a magnetic field or an electric field in order to reduce noises in said test solution.

(10) The instrument described in the above (9) wherein said pressing device applies a constant pressure or a cyclic pressure to said probe.

(11) The instrument described in the above (1) wherein regulatory sequences on at least both ends of the single stranded RNA are fixed on the substrate in the test solution.

(12) The instrument described in the above (1) wherein the single stranded RNA does not migrate in the solution but is linearly fixed on the substrate.

(13) The instrument described in the above (1) wherein the single stranded RNA is in a solution and the displacement of the temperature of the solution during probe scanning is within +/−1° C.

(14) The instrument described in the above (1) wherein at least said subject and the metal probe to which said carbon nanotube is connected have been shielded from an electromagnetic wave with a wavelength of at least 0.1 nanometers or more and 1000 nanometers or less.

(15) The instrument described in the above (1) wherein the number of the probes that are subjected to said reading procedure is two or more.

FIG. 1 illustrates the basic configuration and the operating principles of the instrument of the present invention. A single stranded RNA (13) is fixed on the substrate (mica substrate 19), directly above which a metal probe (10) having a carbon nanotube (11) connected thereto is scanned, wherein one base (12) among the four bases (adenine A, cytosine C, guanine G, and uracil U) (hereinafter referred to as A, C, G, or U) is bound to said carbon nanotube by chemical modification.

Each base has complementarity, and only one specific base generates an attractive force by hydrogen bonding to any one base. Since the attractive force is a minute tension of micronewton or less, disturbances from other bases adjacent at a distance of about two nanometers can be ignored, and thus the reproducibility of the position can be fully secured.

In order to amplify this minute tension, a beam made of a highly elastic metal such as iron that easily bends at a minute load and easily restores to the original state at no load was used, to the end of which a metal probe (10) was mounted.

Accordingly, when a metal probe to the end of which is connected a carbon nanotube that has A bound by chemical modification is being scanned over a single stranded RNA, an attractive force is generated due to complementarity directly above U in the single stranded RNA when encountered, and the metal probe is attracted to the subject RNA due to the attractive force.

Thereby, the beam mounted at the end of the metal probe becomes bent. In order to further amplify the bending, the back side of the beam is irradiated with a beam (17) such as a laser beam emitted from a laser oscillator (14) to cause the mirror reflection of the beam by a reflecting plate (15). By detecting the reflected beam by a detector (16) at a sufficiently far distance, the bending created by a minute attractive force is converted to a reflecting angle of the beam, and thus, a detectably adequate amplification can be made as a difference in the reflection angle of the beam. In this manner, the detection sensitivity of a minute attractive force can be enhanced by converting the minute attractive force into the bending of the beam, and in turn converting the bending of the beam to the reflection angle of the beam.

Figure 2:
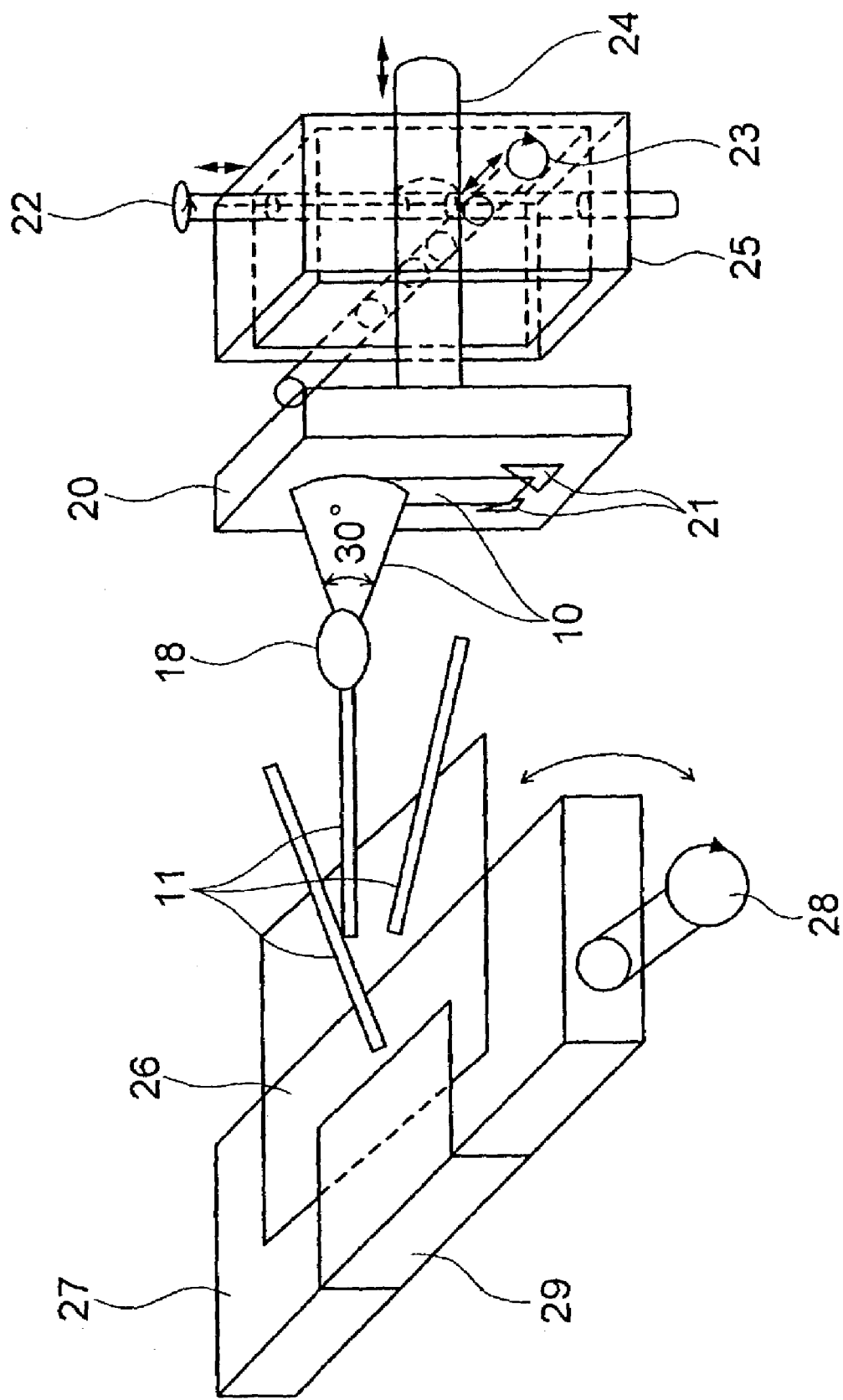
FIG. 2 is a drawing that shows the principle of the device for connecting carbon nanotubes to the metal probe.

In the inside of a focusing beam processing unit as shown in FIG. 2 that accelerates the irradiation of galium ions, a sample chamber was mounted, in which a slanting sample stage (27) and a moving stage (20) facing it were set up. In the unit, a blade (26) (fixed to the stage (27) with a blade pinch (29)) equipped with a carbon nanotube (11) was mounted on the slanting sample stage (27), a metal probe (10) (fixed with a metal probe pinch (21)) is placed on the moving stage (20) facing it, and the metal probe was guided to the end of the carbon nanotube by moving it (10).

The metal probe (10) was mounted on a stage (20) that can move at the triaxial, vertical, horizontal, and height directions, and the facing carbon nanotube was mounted as it is placed on the slanting substrate. Since the focusing ion beam processing unit provides ion images at a magnification equal to secondary electron images in the conventional scanning electron microscope, only one carbon nanotube having the optimum length and direction can be selected by moving the metal probe above the carbon nanotube on the substrate while observing the images.

When the optimum direction cannot be obtained in the positional relationship of the carbon nanotube and the metal probe in the observed region, since the stage (20) that moves the metal probe can independently move to each of triaxial directions of up and down, right and left, and forward and backward by bolts (22, 23, 24) for movement equipped in a bolt-supporting casing (25), the optimum direction of the metal probe and the facing carbon nanotube can be secured by slanting the direction of the carbon nanotube to some degree by means of the bolt (28) for slanting the sample stage.

After the end portion of the metal probe and the end portion of the carbon nanotube were made into contact in this manner, tungusten carbonyl in the gaseous form is blown via a guide tube to the center of the contact area. At the same time, gallium ions accelerated in a beam form are irradiated in a limited manner to the contact area of the end portion of the metal probe and the end portion of the carbon nanotube. This limited irradiation focuses positively charged gallium ions by means of a coiled electromagnet mounted in the focusing ion beam processing unit. By so doing, tungusten carbonyl in the gaseous form is chemically decomposed as in $W(CO)_6 \rightarrow W+6CO$, and the metal tungusten was accumulated as the connecting metal (18) on the contact area of the end portion of the metal probe and the end portion of the carbon nanotube to connect the both of them. CO gas thus generated was released during decomposition from the sample chamber by means of a vacuum pump. After connecting, the metal probe (10) was removed from the focusing ion beam processing unit, and was disconnected from the stage (20) that can move in triaxial directions.

The characteristics of the present invention is to use a highly reliable metal as a connecting material for a connection (18). The fact that by making best use of the minute sizes of a nanometer order of the carbon nanotube, use of a high attaching force due to van der Waals force as a means for identifying bases of a gene is novel, which is believed to provide an unprecedented means to solve technical problems. Thus, fixing by physical absorption cannot offer reliability, and therefore the connection of the carbon nanotube and the probe portion using a metal as described herein a connecting material is a characteristics of the present invention.

Figure 3:
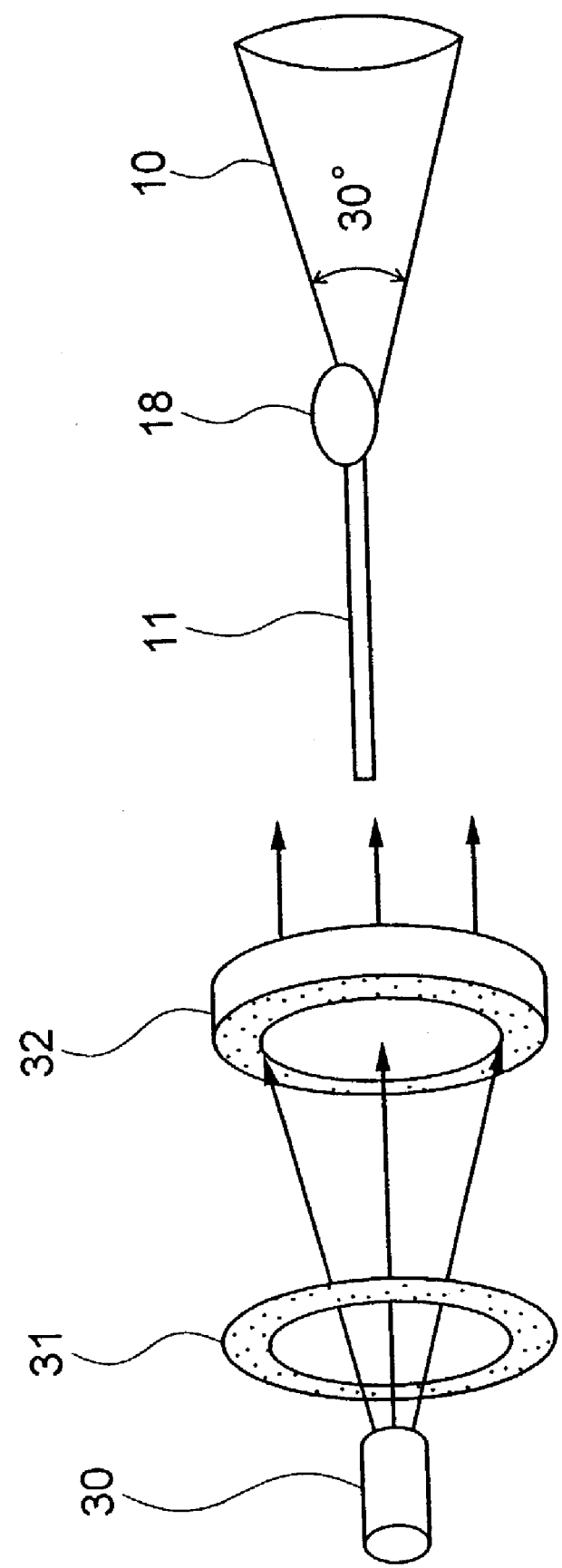
FIG. 3 is a drawing that shows the principle of chemical modification of carbon nanotubes.

In the inside of the electron beam irradiation device, a metal probe (10) to the end of which a carbon nanotube (11) as shown in FIG. 3 was connected is disposed so as to be vertical to the electron beam, and an accelerating voltage of 20 kV which is over the binding energy of carbon of 285 electron volts was applied by electron beam irradiation. An electron beams can be formed by applying a voltage on an electron gun (30), extracting electrons from the electron gun by means of an extracting electrode (31), and forming an electron beam by a focusing electrode (32). Electron irradiation was performed in an atmosphere of $10^{-3}$ Pa or greater in order to prevent its scattering due to the remaining gas. After the electron irradiation, the metal probe to the end of which the carbon nanotube is connected guided to the inside of the chamber filled with water vapors thereby to form —COOH groups at the region where the C—C covalent bond was cleaved of the end portion of the carbon nanotube by electron beam irradiation. Although the carbon nanotube is a hydrophobic substance, it is known to turn hydrophilic by forming —COOH groups on the surface thereof. Then, the hydrophilic carbon nanotube was adjusted to pH 8, and immersed in an aqueous solution in which nucleotides are dispersed for 2 hours to effect the chemical modification of nucleotides to carbon nanotubes.

Figure 4:
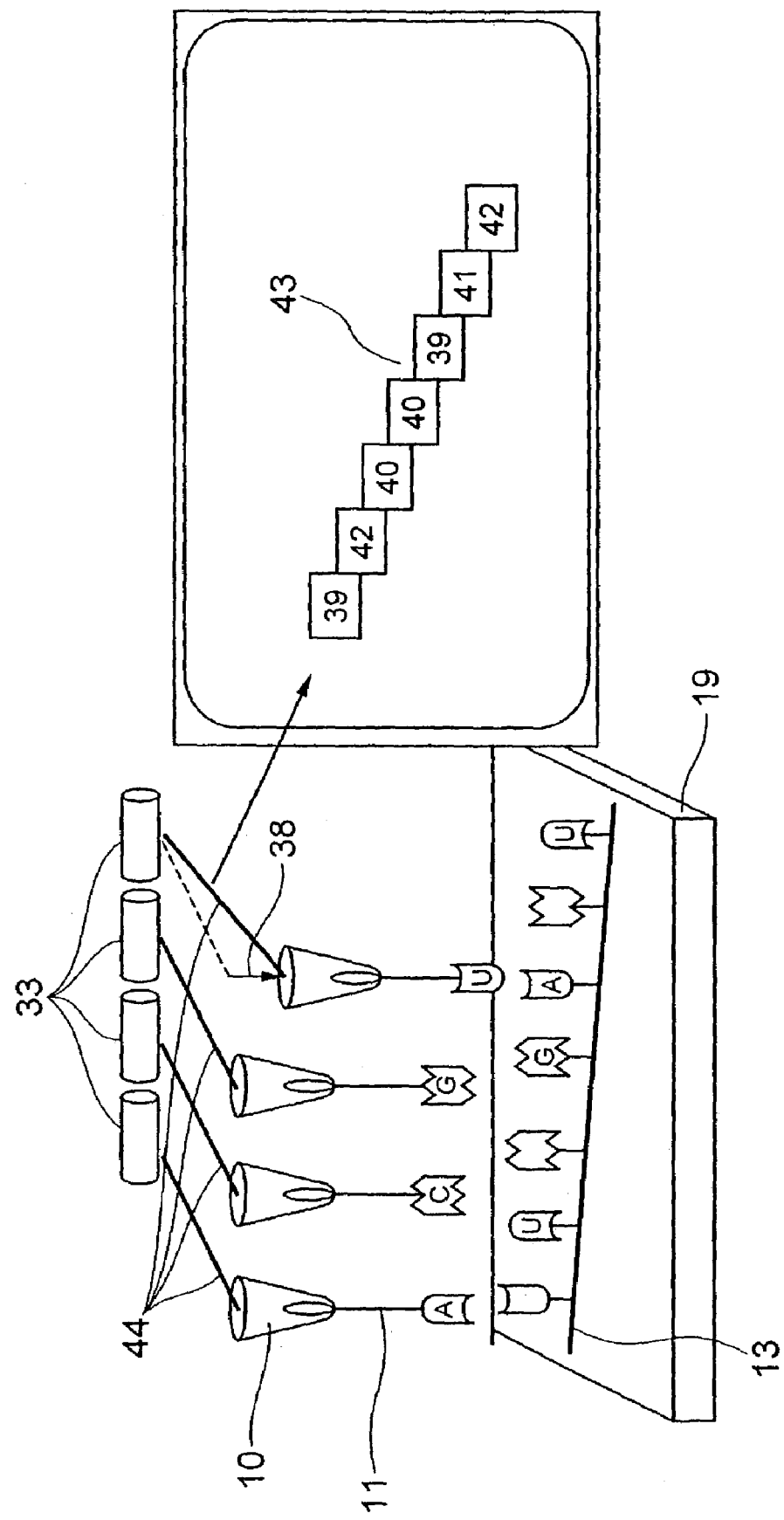
FIG. 4 is a schematic drawing of a system that clarifies all base sequences in RNA.

As shown in FIG. 4, the reading of the gene sequence in RNA by the scanning probe was performed by the reading instrument. RNA (13) is placed on a mica substrate (19) with a smooth surface, and reading was performed using each base bound to a separate metal probe by chemical modification via the carbon nanotube (11). The metal probe (10) was disposed at the end portion of a commercially available cantilever (44) with a spring constant kz=3 N/m mounted to the metal probe-supporting part (33), and the optimum setting of the probe-sample distance and the adjustment of laser beam axes were performed by the conventional method. By the probe scanning of one micrometer square, to uracil U, a complementary base adenine bound to the metal probe via the carbon nanotube only generates an attractive force due to hydrogen binding, which was detected as a point showing the mechanical bending (38) of the metal probe and was displayed as a singular point (42) on a two-dimensional image. For each of four nucleotides, signals due to an attractive force could be detected for the one complementary to a different specific base of four bases in the subject RNA. This means to clarify the position of bases in the subject RNA for each base, and by superimposing the singular point on each two-dimensional images, the base sequence in the subject RNA can be determined. In FIG. 4, assuming that the position of adenine, guanine, cytosine, or uracil that was detected by uracil, cytosine, guanine, or adenine, respectively, bound to the metal probe via the carbon nanotube is 39, 40, 41, or 42, respectively, the base sequence is displayed as shown in 43 by synthesizing the positions of the four bases on the same image.

As hereinabove described, the reading instrument of the present invention makes it possible to read the base sequence in RNA which was conventionally thought to be impossible by connecting the bases at the end portion of the metal probe via a binder of a nanometer order having a strong binding affinity for organic functional groups such as a carbon nanotube on the end portion of the metal probe.

In the conventional DNA sequencers, double stranded DNA that constitutes chromosome was subjected to phased digestion with restriction enzymes to cleave to specific lengths, fluorophores were modified to the end portion, which was subjected to electrophoresis to estimate the length of the cleaved DNA from the length of the time required to migrate a certain distance. Since the base at the end portion is only known, there was a question in the precision of computing by a large scale computer when said phased cleavage is resynthesized. However, the present invention does not only provide the base information of the end portion of the DNA that was cleaved in phases, but all of the base sequence information in the inside of the cleaved DNA. Thus, it obviates the need of computing the precision of base sequence information by large scale computers. There are no problems as variation in fluorescence emission in DNA chips, either. Furthermore, if all base sequences can be read from the RNA having gene information, it becomes easier to determine the entire base sequence of the original DNA using its complementarity. If the entire base sequence of DNA is known, it becomes possible to trace the position of DNA back to the chromosome. Furthermore, the present invention can be used for analyzing polymorphism and functions derived from gene sequences such as dominant differences in the shapes and functions of the living body that occurs by the difference in only one base in a specific DNA sequence in the chromosome.

What is claimed is:

1. An instrument comprising attractive force-generating probes each comprising carbon nanotubes, a detecting part for detecting the attractive force generated between a sample to be detected and said attractive force-generating probes as distortion, an amplifying part for amplifying said distortion, a recording part for recording the distortion signal from said amplifying part, and a display part for displaying the information recorded in said recording part, wherein said carbon nanotube has a chemical functional group that modifies an end of said carbon nanotube and is one of a plurality of bases of a DNA as said sample to be detected.

2. The instrument of claim 1 wherein said carbon nanotube is connected to said probe part comprising a connecting material consisting mainly of a rare metal selected from the group consisting of tungusten, nickel, iron, cobalt, and gold, and an allow thereof.

3. The instrument of claim 1 wherein said probe part and said carbon nanotube is connected by means of a metal such as gold, platinum, titanium, rhenium, silicon, or tungusten, or a nitride thereof used as a connecting material.

4. The instrument of claim 1 which is designed so that 50% or more of the total length of the probe in which the end of said carbon nanotube is chemically modified may be immersed in a test solution.

5. The instrument of claim 4 wherein said probe has an exterior pressing device that utilizes a magnetic field or an electric field in order to reduce noises in said test solution.

6. The instrument of claim 5 wherein said pressing device applies a constant pressure or a cyclic pressure to said probe.

7. The instrument of claim 1 wherein at least said sample to be detected and the metal probe to which said carbon nanotube is connected have been shielded from an electromagnetic wave with a wavelength of at lease 0.1 nanometers or more an 1000 nanometers or less.

8. The instrument of claim 1 wherein the number of the probes is two or more.

* * * * *